United States Patent [19]
Iida et al.

[11] Patent Number: 5,203,336
[45] Date of Patent: Apr. 20, 1993

[54] ULTRASONIC IMAGING APPARATUS

[75] Inventors: Atsuo Iida; Takuya Noda, both of Kawasaki, Japan

[73] Assignee: Fujitsu Ltd., Kawasaki, Japan

[21] Appl. No.: 846,334

[22] Filed: Mar. 6, 1992

[30] Foreign Application Priority Data

Mar. 8, 1991 [JP] Japan .................................. 3-42134

[51] Int. Cl.⁵ .............................................. A61B 8/12
[52] U.S. Cl. ........................... 128/660.06; 128/660.07; 128/661.01; 73/597; 73/625
[58] Field of Search ....................... 128/660.06, 660.07, 128/661.01; 73/597, 625, 609

[56] References Cited

U.S. PATENT DOCUMENTS

| | | | |
|---|---|---|---|
| 4,830,015 | 5/1989 | Okazaki | 128/660.06 |
| 5,113,866 | 5/1992 | Hassler et al. | 128/661.01 |

*Primary Examiner*—William E. Kamm
*Assistant Examiner*—George Manuel
*Attorney, Agent, or Firm*—Staas & Halsey

[57] ABSTRACT

An ultrasonic imaging apparatus for obtaining a tomogram image of an object to be diagnosed on a monitor is provided. The apparatus includes electroacoustic transducers, a phasing unit, a phase detection unit, a reference signal generating unit, and an adding unit. Electroacoustic transducers are provided in a lie along a surface of the object, emit ultrasonic waves to the object, detect the ultrasonic waves reflected therefrom, and convert them to electric signals as detection signals; a phasing unit is operatively connected to the electroacoustic transducers for receiving the detection signals, delaying them in accordance with distance between the electroacoustic transducers and the object, and phasing them to match the phase of detection signals. In addition, a phase detection unit is operatively connected to the electroacoustic transducers and a phasing unit for detecting the error of phase contained in the detection signals output from the electroacoustic transducers or the phasing unit, wherein the amount of delay previously set in the phase unit is corrected in accordance with the error; a reference signal generating unit is operatively connected to the phase detection unit for supplying a reference signal having the same frequency as that of the detection signal thereto; and an adding unit is operatively connected to the phasing unit to accumulate the detection signals phased by the phasing unit.

4 Claims, 11 Drawing Sheets

ULTRASONIC IMAGING APPARATUS

BACKGROUND OF THE INVENTION

1. Field of the Invention

The present invention relates to an ultrasonic imaging apparatus for obtaining a tomogram image of an object by using ultrasonic waves. The present invention is used mainly as a medical instrument for diagnosis.

2. Description of the Related Art

Recently, an ultrasonic imaging apparatus is widely used as a medical instrument for obtaining a tomogram image of an object, for example, internal organs of a human body. Basically, the ultrasonic image apparatus has a plurality of electroacoustic transducers aligned along the surface of the object. The electroacoustic transducers emit ultrasonic waves to the object and detect the ultrasonic waves reflected therefrom. The detected ultrasonic waves are added to each other after a phasing process (i.e., matching all phases of detection signal) in accordance with a predetermined delay process for ultrasonic waves to obtain the phased detection signal, i.e., strengthened detection signal. After the above processes, it is possible to obtain an image signal focused at one particular point in the object. When electrically scanning the electroacoustic transducers, the focused point is straightly scanned so that it is possible to obtain the tomogram image of the object. Further, when controlling the time difference (below, the amount of delay), the focused point is curvedly scanned so that it is possible to obtain the tomogram image of the object.

In this case, a propagation speed of the ultrasonic wave is slightly different within the object caused by the medium forming the object. That is, the propagation speed for the adipose tissue is different from that of the muscle tissue. Accordingly, the delay process is very important for adjusting the different propagation speed of the ultrasonic waves to obtain the clear tomogram image of the object. That is, when the propagation speed is not uniform within the object, it is impossible to obtain a clear tomogram image of the object. Accordingly, it is necessary to provide the means for preventing the deterioration of the tomogram image caused by nonuniformity of the propagation speed of the ultrasonic waves within the object.

SUMMARY OF THE INVENTION

The object of the present is to provide an ultrasonic imaging apparatus enabling the prevention of the deterioration of the tomogram image caused by nonuniformity of the propagation speed within the object and enabling a high precision tomogram image by using a very simplified structure.

In accordance with the present invention, there is provided an ultrasonic imaging apparatus for obtaining a tomogram image of an object to be diagnosed on a monitor, including:

electroacoustic transducers provided in a line along a surface of the object, emitting ultrasonic waves to the object, detecting the ultrasonic waves reflected therefrom, and converting them to electric signals as detection signals;

a phasing unit operatively connected to the electroacoustic transducers for receiving the detection signals, delaying them in accordance with the distance between the electroacoustic transducers and the object, and phasing them to match the phase of detection signals;

a phase detection unit operatively connected to the electroacoustic transducers and a phasing unit for detecting the error of phase contained in the detection signals output from the electroacoustic transducers or the phasing unit, wherein an amount of delay previously set in the phase unit is corrected in accordance with the error;

a reference signal generating unit operatively connected to the phase detection unit for supplying a reference signal having the same frequency as that of the detection signal thereto; and an adding unit operatively connected to the phasing unit to accumulate the detection signals phased by the phasing unit;

the phase detection unit further including a calculation unit for calculating a mutual-relation value between the detection signal and the reference signal, and an error detection unit detecting the error of the phase of the detection signals based on the mutual-relation value.

In one preferred embodiment, the reference signal has the same phase as the amount of delay previously set in the phase unit when the phase detection unit detects the detection signals output from the electroacoustic transducers.

In another preferred embodiment, the reference signal has the same phase for all detection signals when the phase detection unit detects the detection signals from the phasing unit.

In still another preferred embodiment, an output signal from the adding unit is used as the reference signal.

DESCRIPTION OF THE PREFERRED EMBODIMENTS

Before describing the preferred embodiments, an explanation will be given of a conventional ultrasonic imaging apparatus.

Figure 1:
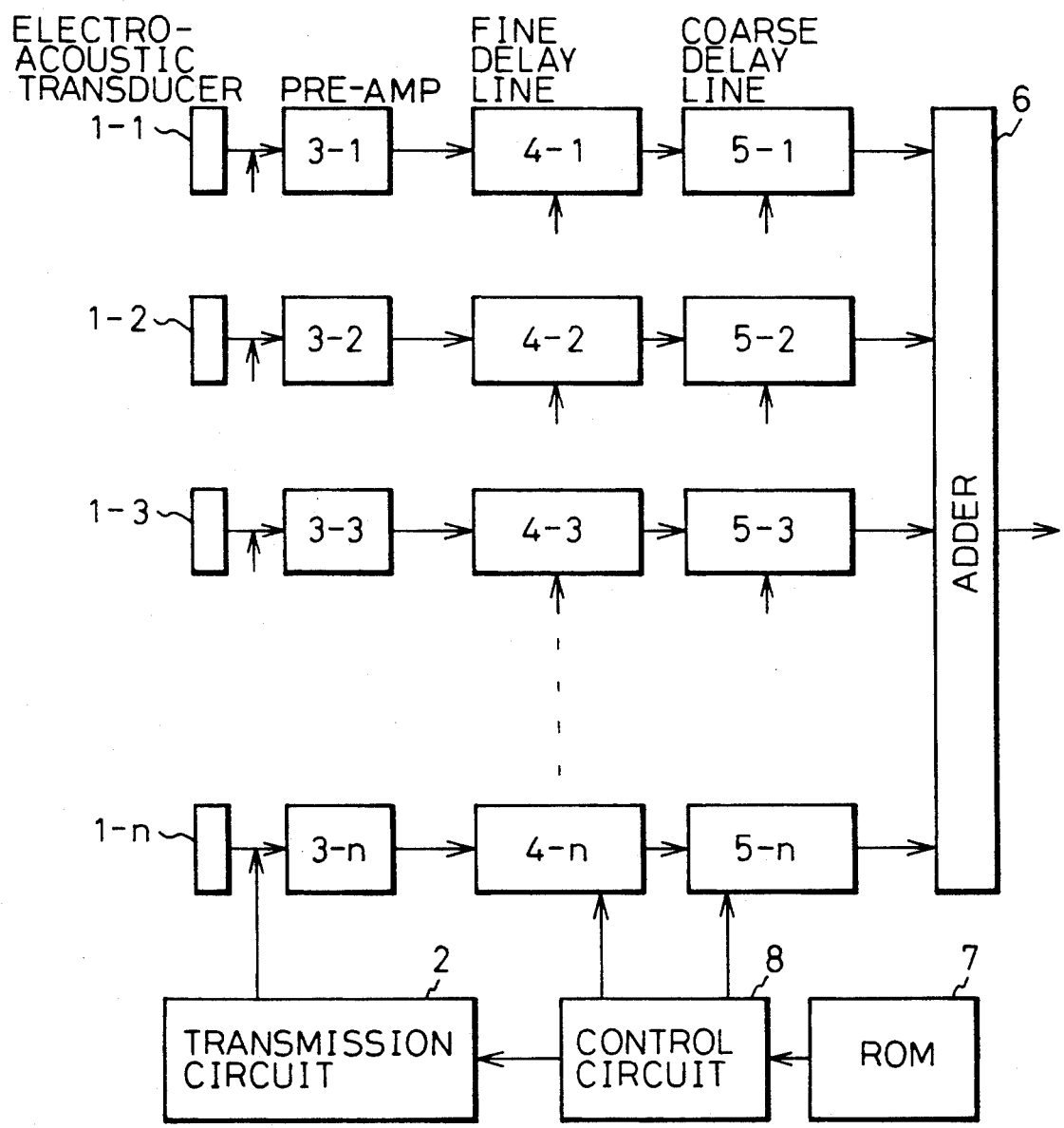
FIG. 1 is a schematic block diagram of a conventional ultrasonic imaging apparatus.

FIG. 1 is a schematic block diagram of a conventional ultrasonic imaging apparatus. This ultrasonic imaging apparatus is known in the documents, for example, (1) Japanese Unexamined Patent Publication (KOKAI) No. 53-28989, and (2) Japanese Unexamined Patent Publication (KOKAI) No. 54-96286. The former application corresponds to U.S. application (Ser. No. 718,721) by Richard D. Belling, filed on Aug. 30, 1976, and the latter corresponds to U.S. application (Ser. No. 862,454) by Samuel H. Masrak, filed on Dec. 20, 1977.

In FIG. 1, reference numbers 1-1 to 1-n denote electroacoustic transducers, 2 a transmission circuit, 3-1 to 3-n pre-amplifiers, 4-1 to 4-n fine delay lines, 5-1 to 5-n coarse delay lines, 6 an adder, 7 a read only memory (ROM), and 8 a control circuit.

The elecroacoustic transducers 1-1 to 1-n are provided in a line (aligned) along the surface of the object, and the electroacoustic transducers 1-1 to 1-n emit the ultrasonic waves to the object and detect the ultrasonic waves reflected from the object (below, detection signal). The transmission circuit 2 generates electric pulses parallel to the electroacoustic transducers 1-1 to 1-n to control the emission of the ultrasonic waves. The pre-amplifiers 3-1 to 3-n amplify the detection signal from the electroacoustic transducers 1-1 to 1-n. The fine delay lines 4-1 to 4-n are formed by LC (inductor and capacitor) circuits for delaying the detection signal from the pre-amplifier based on an adjustable amount of delay. The coarse delay lines 5-1 to 5-n are also formed by LC circuits for obtaining a fixed amount of delay. By these delay lines, the detection signals are phased. The adder 6 adds all output from the coarse delay lines 5-1 to 5-n to obtain the tomogram of the object. The ROM 7 stores data of the fine and coarse amount of delay previously determined in accordance with the difference of the distance between each electroacoustic transducer and the focused point. The amount of delay is shown by the formula (1) explained hereinafter. The control circuit 8 determines the fine delay amount and the coarse delay amount in accordance with the data stored in the ROM 7.

Figure 2:
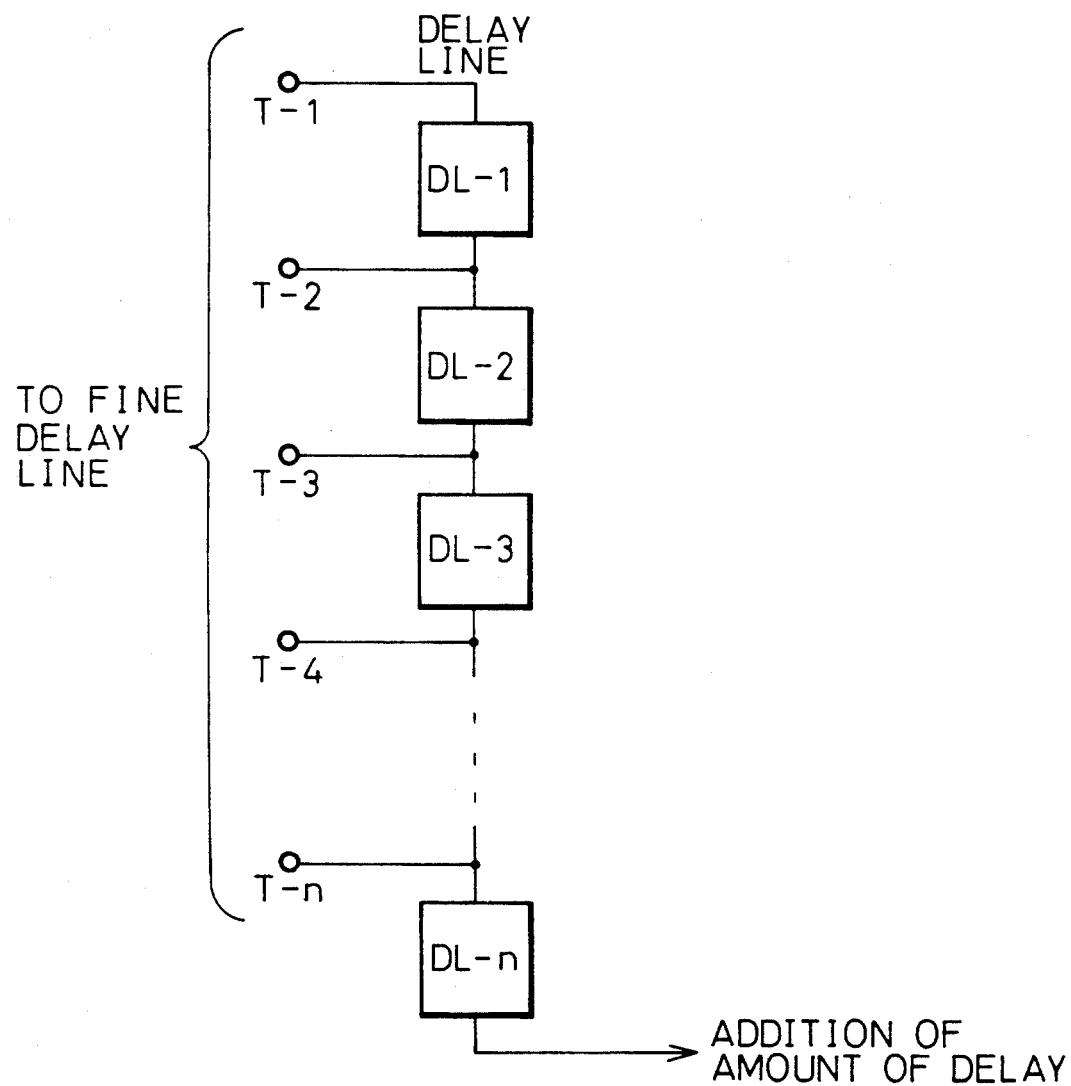
FIG. 2 is a schematic block diagram of a conventional coarse delay line shown in FIG. 1.

FIG. 2 is a schematic block diagram of a conventional coarse delay line shown in FIG. 1. The coarse delay line is formed by a fixed delay lines DL-1 to DL-n each having taps T-1 to T-n connected to the fine delay lines 4-1 to 4-n to simultaneously perform the delay and adding operation. In this case, each of delay lines DL-1 to DL-n has the same amount of delay $\Delta t$ so that all amounts of delay Ti of the fixed delay line can be expressed by the formula (2) as explained hereinafter. Since all amounts of delay are accumulated by these delay lines DL-1 to DL-n, it is possible to delete the adder 6 shown in FIG. 1.

Figure 3:
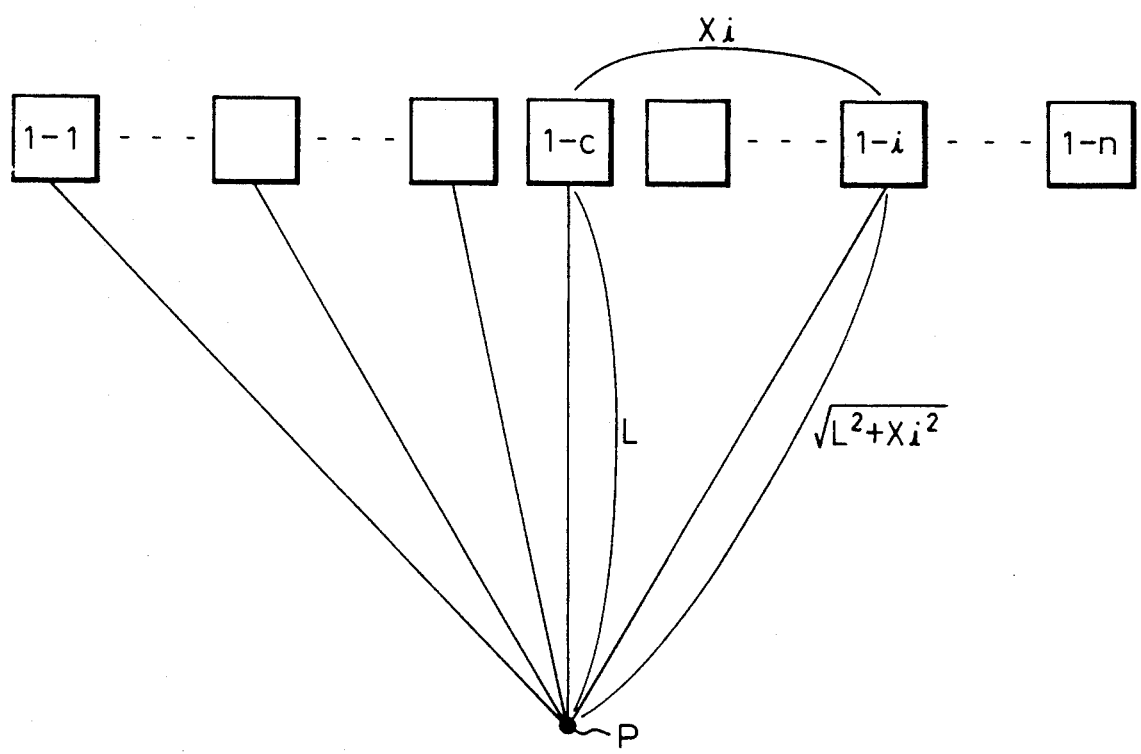
FIG. 3 is a view for explaining the amount of delay.

FIG. 3 is a view for explaining the amount of delay. 1-1 to 1-n denote electroacoustic transducers, 1-c denotes a center transducer and 1-i denotes the transducer away from the center transducer 1-c by distance Xi. "P" denotes a point focused by emission of all transducers 1-1 to 1-n and this focused point is located by distance L from the center transducer 1-c. In this case, the amount of delay $\tau i$ at the transducer 1-i is given as the following formula.

$$\tau i = \tau 0 + (\sqrt{L^2 + Xi^2} - L)/C \qquad (1)$$

Where, C denotes a speed of ultrasonic waves, and $\tau 0$ denotes a constant value, the value $\tau i$ of which becomes positive.

Accordingly, the detection signal from the electroacoustic transducer 1-i is phased by the amount of delay $\tau i$. Similarly, all detection signals are phased by the corresponding amount, and after a phasing process by the delay lines, all phased detection signals are added by the adder 6. As is obvious from the formula (1), since the distance between the electroacoustic transducer 1-i and the focused point P is longer than the distance between the electroacoustic transducer 1-c and the focused point P, the amount of delay of the transducer 1-i is set to a value smaller than that of the transducer 1-c. As explained above, when electrically scanning the electroacoustic transducers, the focused point is straightly scanned so that it is possible to obtain the tomogram of the object. When controlling the amount of delay, the focused point is curvedly scanned so that it is possible to obtain the tomogram of the object.

Further, the amount of delay Ti at each coarse delay line 5-1 to 5-n is expressed by the following formula.

$$Ti = \text{int}(\tau i/\Delta t) \times \Delta t \qquad (2)$$

Where, $\Delta \tau$ is a fixed delay amount for unit length of the coarse delay line (so-called quantumaized error), and "int" is a positive integer.

The amount of delay "ti" at each fine delay line 4-1 to 4-n is expressed by the following formula.

$$ti = \tau i - Ti \qquad (3)$$

The amount of delay previously determined by the above formula (2) and (3) is stored in the memory (ROM) 7. The control circuit 8 reads the amount of delay from the memory to control the fine and coarse delay line.

Figure 4:
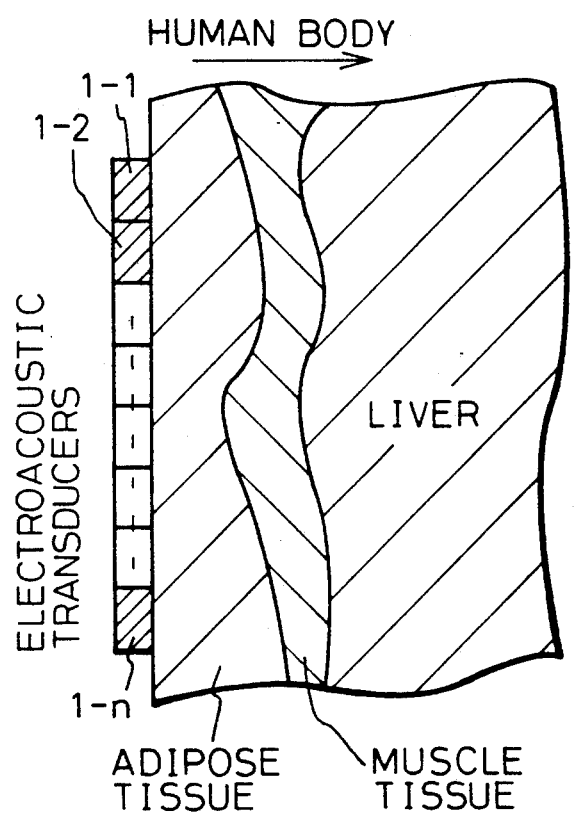
FIG. 4 is a schematic sectional view of an object.

FIG. 4 is a schematic sectional view of an object, for example, a human body. The electroacoustic transducers 1-1 to 1-n are aligned on the surface of the human body to diagnose the internal organ, for example, a liver. Of course, the adipose tissue and the muscle tissue exist between the transducer and the liver. In this case, the propagation speed of the ultrasonic waves for the adipose tissue is different from that of the muscle tissue. In general, the propagation speed in the muscle and liver tissues is 1570 per second, and the propagation speed in the adipose tissue is 1480 per second. As is obvious, the former is faster than the latter within the human body. Further, as shown in the drawing, each tissue has a different thickness. Accordingly, this is the reason for nonuniformity of the propagation speed in the object so that it is very difficult to obtain a clear and precise tomogram image of the object.

Figure 5:
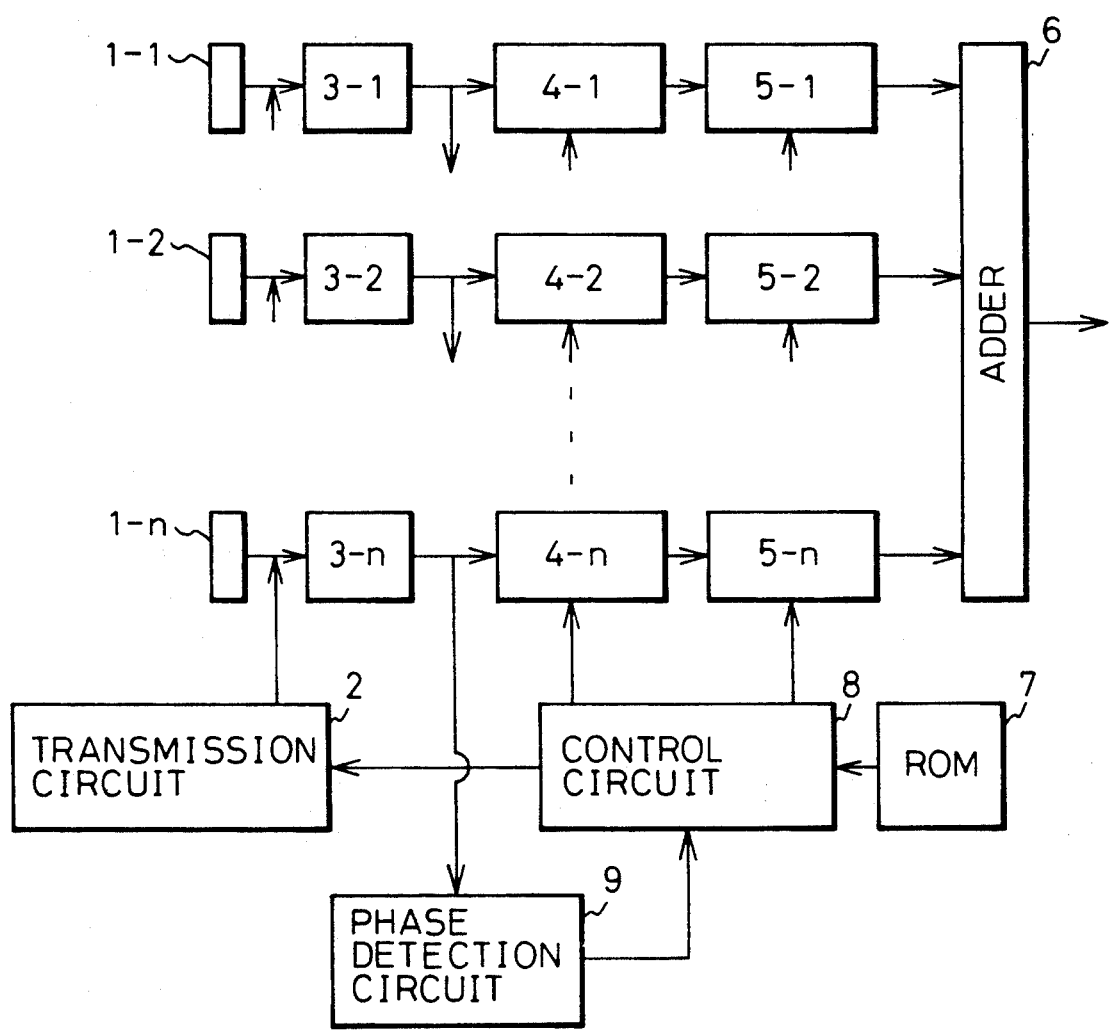
FIG. 5 is a schematic block diagram of another conventional ultrasonic imaging apparatus.

FIG. 5 is a schematic block diagram of another conventional ultrasonic imaging apparatus. This apparatus is superior to the structure shown in FIG. 1 in solving the above explained problem. The reference numbers used in FIG. 1 are attached to the same components in this drawing. In FIG. 5, reference number 9 denotes a phase detection circuit. The phase detection circuit 9 is added to the structure shown in FIG. 1, and detects the phase of the detection signal of each electroacoustic transducer 1-1 to 1-n and supplies resultant data to the control circuit 8 to adjust the amount of delay.

Some phase detection circuits are known in the documents, for example, "U.S. Pat. No. 4,817,614", "U.S.

Pat. No. 4,471,785", and "U.S. Pat. No. 4,484,477". The phase detection shown in these documents is explained in detail hereinafter.

Figure 6:
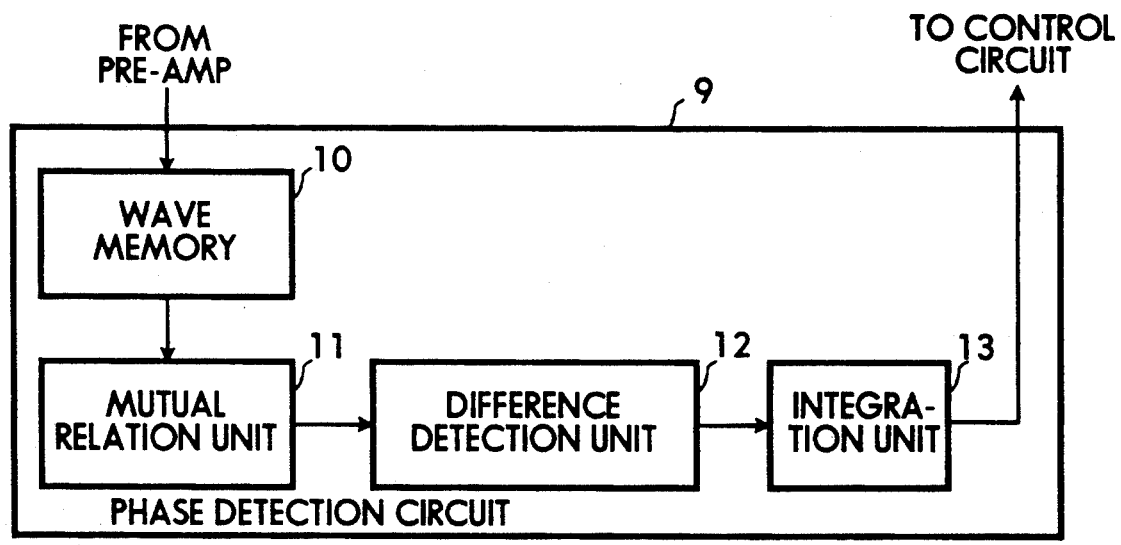
FIG. 6 is a detailed block diagram of a phase detection circuit shown in FIG. 5.

FIG. 6 is a detailed block diagram of the phase detection circuit shown in FIG. 5. In FIG. 6, reference number 10 denotes a wave memory, 11 a mutual-relation unit, 12 a difference detection unit, and 13 an integration unit. The wave memory 10 temporarily stores the detection signal from the pre-amplifier 3-1 to 3-n. The mutual-relation unit 11 calculates a mutual-relation value by selecting the detection signals of two adjacent electroacoustic transducers from the wave memory 10. The difference detection unit 12 detects the maximum time difference of the mutual-relation value calculated by the mutual-relation unit 11. The integration unit 13 integrates the time difference detected by the difference detection unit 12, determines the amount of delay for all detection signals, and informs the control circuit 8 of the amount of the delay.

In this case, if the wave memory 10 is formed by a digital memory, it is necessary to provide an analog-to-digital converter. Further, if the wave memory is formed by an analog memory, it is necessary to provide a sample-holding circuit. However, these circuits are omitted to simplify the explanation.

Figure 7:
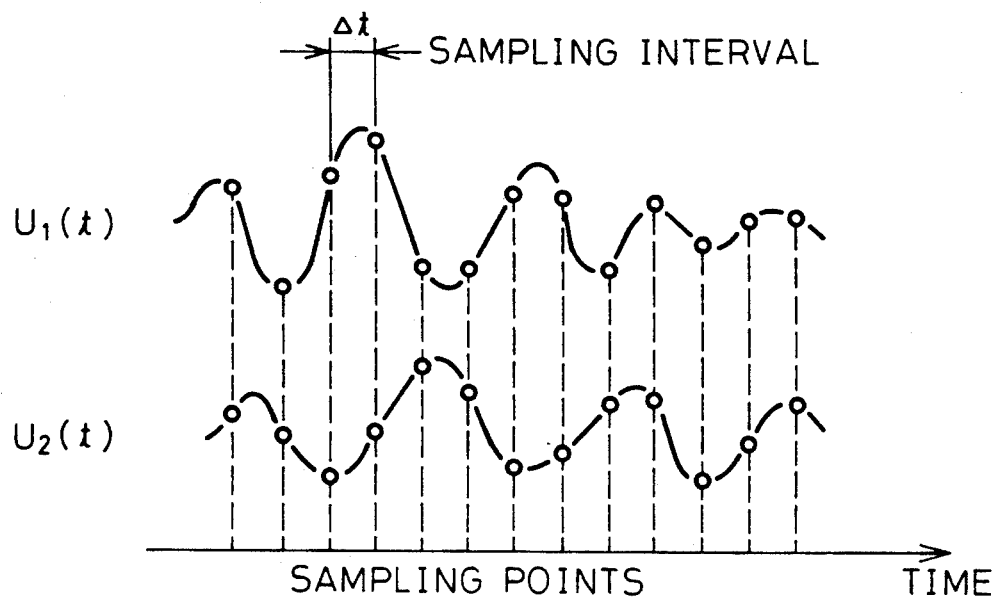
FIGS. 7 and 8 are graphs explaining the mutual-relation value determined by the phase detection circuit shown in FIG. 6.
Figure 8:
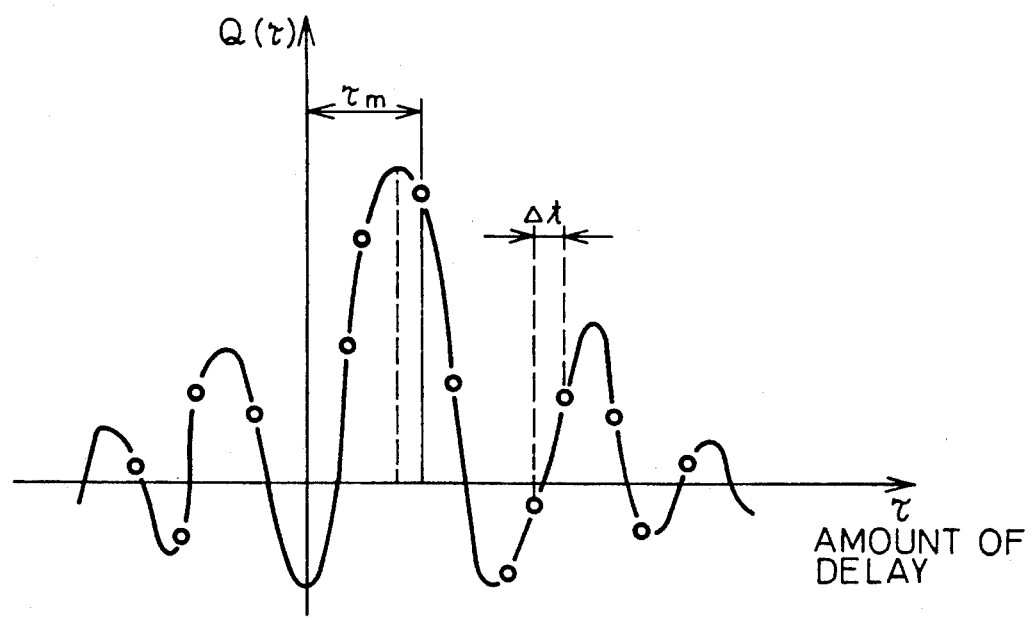

FIGS. 7 and 8 are graphs explaining the mutual-relation value determined by the phase detection circuit shown in FIG. 6. In these drawings, $u_1(t)$ and $u_2(t)$ denote the detection signals from the two adjacent electroacoustic transducers, $\Delta t$ denotes a sampling time interval, $Q(\tau)$ denotes the mutual-relation value, and $\tau m$ denotes the maximum value of the mutual-relation value. The mutual-relation value $Q(\tau)$ is expressed by the following formula.

$$Q(\tau) = \int_{t1}^{t2} u_1(t) u_2(t - \tau) dt \quad (4)$$

There, $t_1$ to $t_2$ denote calculation time.

Based on the above formula, the mutual-relation unit 11 calculates the mutual-relation value $Q(\tau i)$ at each time difference (i.e., amount of delay) $\tau i$, the difference detection unit 12 detects the maximum time difference of the mutual-relation value $\tau m$. Further, the integration unit 13 integrates the time difference, determines the amount of delay for all detection signals, and informs the control circuit 8.

As another known document, "U.S. Pat. No. 4,835,689" discloses a method for correcting the deterioration of the image caused by nonuniformity of the propagation speed within the object by using a quadrature modulation. Further, "Phase-Aberration Correction Using Signals From Point Reflectora and Diffuse Scatterres" by S. W. Flax and M. O'Donnel, IEEE Vol. 35, No. 6, November 1988, pp 758–767. This document discloses an error of ultrasonic waves emitted from the electroacoustic transducer.

There are, however, some problems in the above conventional ultrasonic imaging apparatus shown in FIG. 5. As explained above, the phase detection circuit 9 performs a calculation of the mutual-relation value of the detection signal to determine the amount of delay that prevents the deterioration of the tomogram image caused by the nonuniformity of the propagation speed within the object.

As shown in FIG. 8, however, since the mutual-relation value is calculated from the time sampling interval $\Delta t$ of the detection signal, the amount of delay determined by the phase detection circuit 9 includes an error contained in the time sampling interval $\Delta t$. That is, since the amount of delay depends on the sampling time interval $\Delta t$, the error in the sampling time interval $\Delta t$ is included in the amount of delay determined by the phase detection circuit 9. Further, each error is accumulated when the integration unit 12 determines the amount of delay for all detection signals so that it is very difficult to determine the precise amount of delay of the detection signal from the electroacoustic transducers 1-1 to 1-n.

The above document of "S. W. Flax and M. O'Donnel" discloses a very high sampling frequency in solving the above problem. That is, in general, when the frequency of the ultrasonic waves is 3.5 MHz, the sampling time interval $\Delta t$ is set to 20 MHz. However, in "S. W. Flax and M. O'Donnel", the sampling time interval $\Delta t$ is set to a very high frequency, for example, 100 MHz to prevent an error accumulated in the sampling time interval.

However, as is obvious, the higher the sampling frequency, the more sampling data. Accordingly, it is necessary to provide a very large and complex phase detection circuit to process bulky sampling data. That is, the above conventional art requires bulky hardware, particularly, a very large and complex phase detection circuit.

Therefore, the object of the present invention is to provide an ultrasonic imaging apparatus that can prevent the deterioration of the tomogram image caused by nonuniformity of the propagation speed within the object and can achieve a high precision tomogram image with a very simplified structure.

Figure 9:
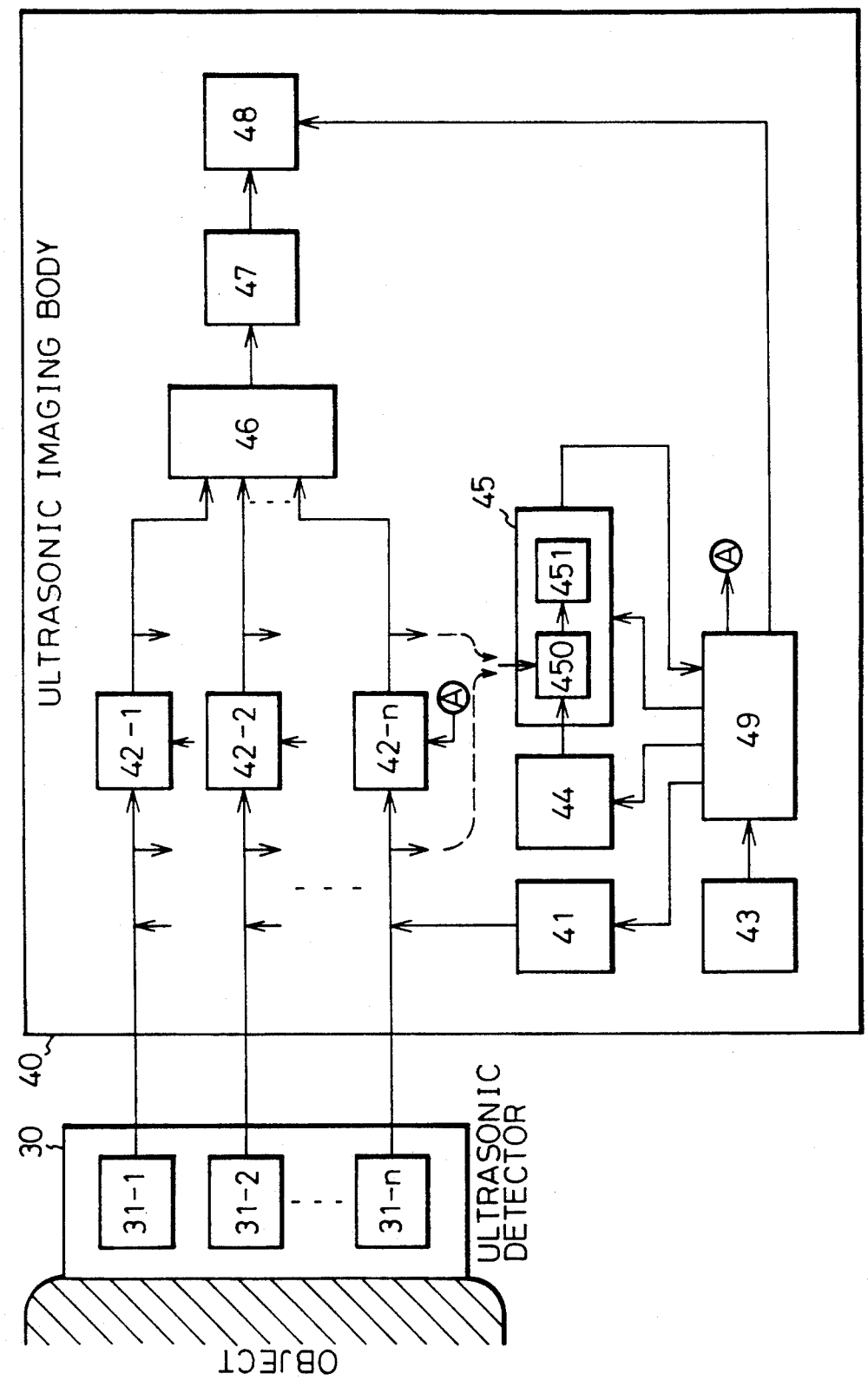
FIG. 9 is a schematic block diagram of an ultrasonic imaging apparatus according to the present invention.

FIG. 9 is a schematic block diagram of a ultrasonic imaging apparatus according to the present invention. Briefly, the feature of the present invention lies in a reference signal previously determined. That is, the reference signal is determined based on the amount of delay depending on the distance between the electroacoustic transducer and the point to be focused in the object. Further, this reference signal is compared with the signal delayed by the medium, for example, the adipose tissue and the muscle tissue of the object. In this case, the necessary amount of delay is adjusted by a phasing means under the control of a phase detection circuit as explained in detail hereinafter.

In FIG. 9, reference number 30 denotes an ultrasonic detector formed by a plurality of electroacoustic transducers 31-1 to 31-n, and 40 a body of an ultrasonic imaging apparatus. The electroacoustic transducers 31-1 to 31-n are provided in a line (aligned) along the object to be diagnosed. The electroacoustic transducers 1-1 to 1-n emit the ultrasonic waves to the object, detect them reflected therefrom, and convert them to electric signals as the detection signal. The body 40 is formed by a transmission unit 41, phasing units 42-1 to 42-n, a storage unit 43, a reference signal generating unit 44, a phase detection unit 45, an adder 46, a display signal generating unit 47, a display unit 48, and a control unit 49. The phase detection unit 45 further comprises a calculation unit 450 and an error detection unit 451.

The transmission unit 41 supplies electric pulses parallel to the electroacoustic transducers 31-1 to 31-n to control the emission of the ultrasonic waves. That is, the electroacoustic transducers 31-1 to 31-n emit ultrasonic waves to the object to the time of the electric pulses. Each phasing unit 42-1 to 42-n performs the phasing process by delaying the detection signal from the corresponding electroacoustic transducer in accordance with the distance between the electroacoustic transducer and the object. The storage unit 43 stores the amount of delay previously determined based on the distance between two adjacent electroacoustic transducers and the object.

The reference signal generating unit 44 generates the reference signal having the same frequency as the detection signal. In the phase detection unit 45, the calculation unit 450 calculates the mutual-relation value between the reference signal and the detection signal, and the error detection unit 451 detects the error of phase caused by nonuniformity of the detection signal in accordance with the mutual-relation value.

The adder 46 adds all detection signals phased by the phasing units 42-1 to 42-n. The display signal generating unit 47 generates the display signal after converting the brightness of the signals added by the adder 47. The display unit 48 displays the tomogram image of the object. Further, the control unit 49 controls all operations in the above units 41, 43, 44, and 45.

In this case, the reference signal generating unit 44 preferably generates two kinds of reference signals. That is, when the phase detection circuit 45 uses the detection signal from the electroacoustic transducers 31-1 to 31-n, the reference signal generating unit 44 generates a reference signal having a phase corresponding to the amount of delay determined in the phasing unit. When the phase detection circuit 45 uses the detection signal from the phasing unit 42-1 to 42-n, the reference signal generating unit 44 generates the reference signal having the same phase as all detection signals.

In the present invention, when using the detection signal from the electroacoustic transducers 31-1 to 31-n, the error detection unit 450 calculates the mutual-relation value between the above detection signal from the electroacoustic transducers and the reference signal. The error detection unit 451 obtains a maximum time difference $\tau m$, determines the amount of the delay for the detection signal, and calculates the difference value between the amount of delay determined thereby and the amount of delay stored in the storage unit 43. As a result, the error detection unit 451 can detect the amount of delay caused by nonuniformity of the propagation speed within the object. The control unit 49 performs a correction of the amount of delay already set in the phasing units 42-1 to 42-n.

In this case, when the reference signal is set to the same phase for the amount of delay in the phasing units 42-1 to 42-n, the error detection unit 451 directly detects the amount of delay without calculation of the above difference.

Further, when using the detection signal from the phasing units 42-1 to 42-n, the error detection unit 450 calculates the mutual-relation value between the detection signal from the phasing units and the reference signal. The error detection unit 451 obtains the maximum time difference $\tau m$ of the mutual-relation value, and detects the error of the phase caused by nonuniformity of the propagation speed. The control unit 49 performs a correction of the amount of delay already set in the phasing unit 42-1 to 42-n.

In the present invention, since the reference signal is used for determining the amount of delay to be set to the phasing unit 42-1 to 42-n, it is not necessary to accumulate the detection signals for obtaining the amount of delay as mentioned in the conventional art. Accordingly, in the present invention, it is possible to determine the amount of delay at the phasing units 42-1 to 42-n without the error accumulated by the sampling time interval $\Delta t$. As a result, the ultrasonic imaging apparatus according to the present invention can prevent deterioration of the tomogram image caused by nonuniformity of the propagation speed within the object so that it is possible to provide a high precision tomogram image under the ultrasonic imaging apparatus having a very simplified structure.

Figure 10:
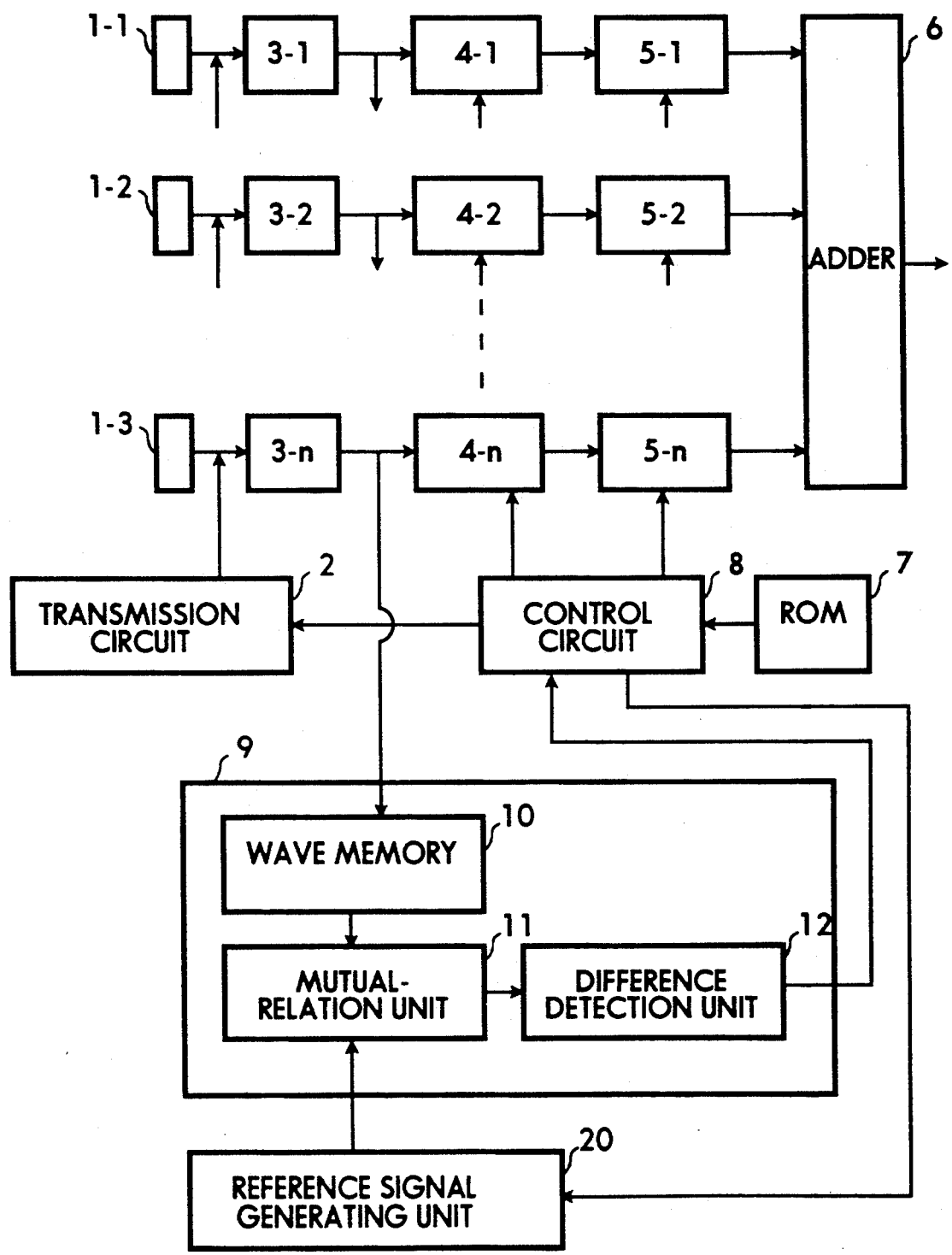
FIG. 10 is a schematic block diagram of the ultrasonic imaging apparatus according to an embodiment of the present invention.

FIG. 10 is a schematic block diagram of the ultrasonic imaging apparatus according to an embodiment of the present invention. The reference numbers used in FIG. 1 are attached to the same components in this drawing. In FIG. 10, reference number 9 denotes the phase detection circuit formed by the wave memory 10, the mutual-relation unit 11 and the difference detection unit 12. Further, reference number 20 denotes the reference signal generating unit. In this embodiment, only one phase detection circuit is provided in the apparatus, and the wave memory 10 temporarily stores the detection signals from all pre-amplifiers 3-1 to 3-n.

As shown in the drawing, the phase detection unit circuit 9 does not comprise the integration unit 13 shown in FIG. 6, and the amount of delay detected by the difference detection unit 12 is directly input to the control circuit 8. Further, the reference signal generating unit 20 receives the output of the control circuit 8 and outputs the reference signal to the mutual-relation unit 11. In this case, the reference signal has the same frequency as that of detection signal of the ultrasonic waves, and the reference signal is input to the mutual-relation unit 11. The mutual-relation unit 11 calculates the mutual-relation value between the reference signal and the detection signal read out from the wave memory 10. The difference detection unit 12 detects the time difference, i.e., the amount of delay, indicating the maximum value of the mutual-relation value calculated by the mutual-relation unit 11, and outputs the amount of delay to the control circuit 8.

When the control circuit 8 receives the amount of delay, it determines the amount of delay to the fine delay lines 4-1 to 4-n to correct nonuniformity of the propagation speed. That is, when the difference detection unit 12 calculates the difference value (the amount of delay) between the amount of delay informed by the difference detection unit 12 and the amount of delay ($\tau i$) indicated by the formula (1), the control circuit 8 receives the amount of delay from the difference detection unit 12 and determines the amount of delay to the fine delay lines 4-1 to 4-n to correct non-uniformity of the propagation speed of the ultrasonic waves in the object. Accordingly, the amount of delay previously set to the fine delay lines is corrected by the amount of delay determined by the control circuit 8.

In the above explanation, the reference signal has the same phase as that of all detection signals. Further, as another embodiment, it is possible to change the phase of the reference signal in accordance with the phase of the detection signals. As a result, the difference detection unit 12 directly detects the amount of delay to be corrected, and the control circuit 8 does not need to perform the calculation of the difference value.

Figure 11:
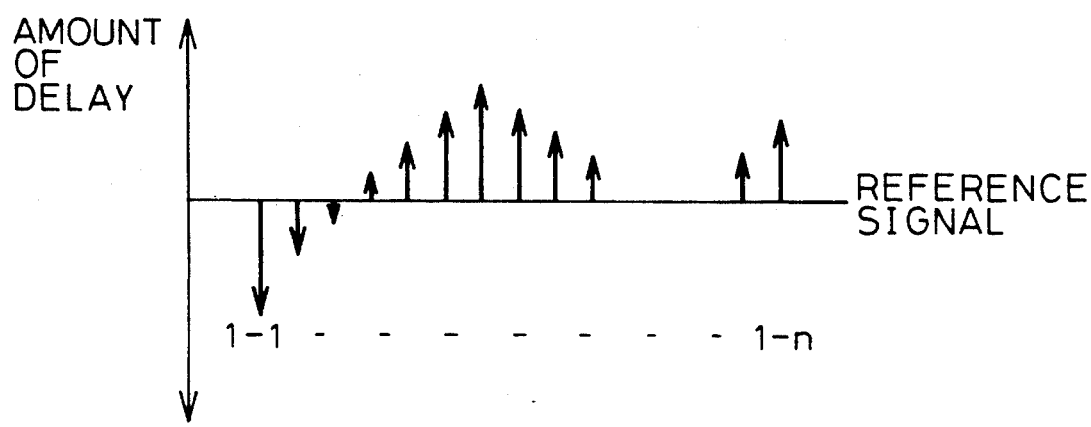
FIG. 11 is a graph explaining the relationship between the amount of delay and the reference signal.

FIG. 11 is a graph explaining the relationship between the amount of delay and the reference signal. This reference signal is common to all detection signals detected by the electroacoustic transducer 1-1 to 1-n. Each arrow line denotes the amount of delay in each of electroacoustic transducers 1-1 to 1-n. The phase detection circuit 9 detects the amount of delay of the detection signal in accordance with the reference signal generated by the reference signal generating unit 20. Accordingly, it is not necessary to provide the conventional integration unit 13 shown in FIG. 6, and it is possible to determine the amount of delay that is set to the fine delay line without the error accumulated in the integrated values. As a result, it is possible to prevent the tomogram image of the object from deterioration caused by nonuniformity of the propagation speed in the object.

Figure 12:
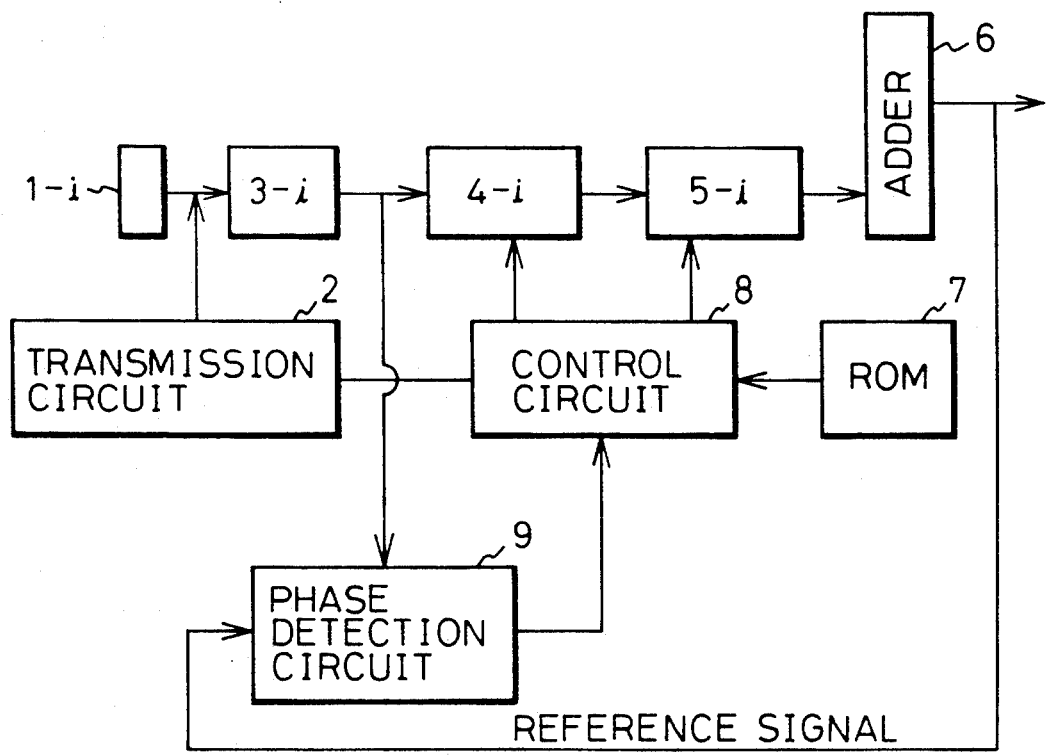
FIG. 12 is a schematic block diagram of the ultrasonic imaging apparatus according to another embodiment of the present invention.

FIG. 12 is a schematic block diagram of the ultrasonic imaging apparatus according to another embodiment of the present invention. Of course, in the drawing, 3-i denotes the pre-amplifiers corresponding to the pre-amplifiers 3-1 to 3-n, 4-i denotes the fine delay lines corresponding to the fine delay lines 4-1 to 4-n, and 5-i denotes the coarse delay lines 5-1 to 5-n. In this embodiment, the output of the adder 6 is used as the reference signal and input to the phase detection circuit 9. In this case, if nonuniformity of the propagation speed is very small, the adder 6 outputs a phased signal. Accordingly, it is possible to use the output of the adder 6 as the reference signal. Therefore, it is possible to delete the reference signal generating unit 20 shown in FIG. 10.

Figure 13:
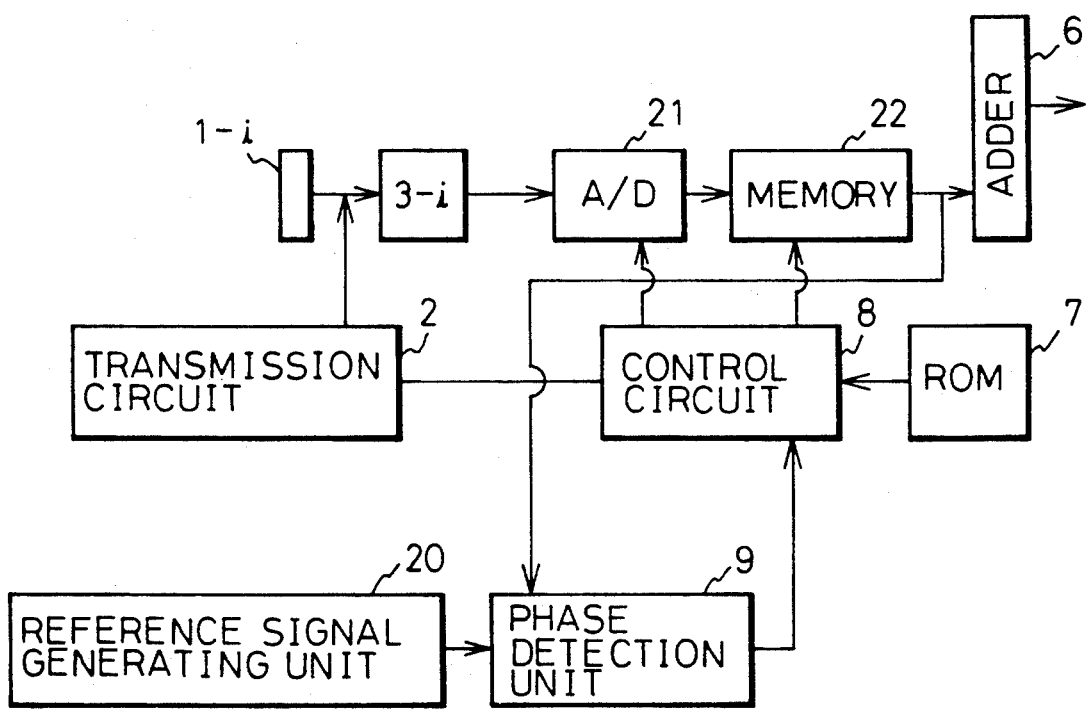
FIG. 13 is a schematic block diagram of the ultrasonic imaging apparatus according to another embodiment of the present invention.

FIG. 13 is a schematic block diagram of the ultrasonic imaging apparatus according to another embodiment of the present invention. In FIG. 13, reference number 21 denotes an analog-to-digital converter, and 22 denotes a memory. In this embodiment, the detection signal from the pre-amplifier 3-1 is converted to a digital value and accumulated in the memory 22. The control circuit 8 controls the read operation from the memory 22. That is, the data to be read from the memory 22 is controlled by the control circuit 8. The read data from the memory 22 is input parallel to the adder 6 and the phase detection circuit 9. In this embodiment, it is necessary to provide the reference signal generating unit 20 to supply the reference signal to the phase detection circuit 9. In this embodiment, since it is possible to obtain the detection signal before the adder 6, the phase detection circuit 9 directly detects the amount of delay to be corrected in accordance with the reference signal. As a result, it is not necessary to perform the calculation of the difference value in the control circuit 8.

Accordingly, an ultrasonic imaging apparatus according to the present invention can prevent deterioration of the tomogram image caused by non-uniformity of the propagation speed within the object and can achieve a high precision tomogram image.

We claim:

1. An ultrasonic imaging apparatus for obtaining a tomogram image of an object having a surface to be diagnosed on a monitor, comprising:
   electroacoustic transducers emitting ultrasonic waves in a line along the surface of the object, and for detecting the ultrasonic waves reflected from the object as reflected waves, and for converting the reflected waves into electric signals as detection signals having a phase and a detection frequency;
   phasing means operatively connected to the electroacoustic transducers for receiving the detection signals, for delaying the detection signals for a delay period as delayed detection signals responsive to a distance between the electroacoustic transducers and the object, and for phasing the delayed detection signals for a phase period to match the phase of the detection signals as phased detection signals having a phased frequency;
   phase detection means operatively connected to the electroacoustic transducers and the phasing means for detecting an error of phase between a reference signal and one of the detection signals output from the electroacoustic transducers and the phased detection signals output from the phasing means, and for correcting the delay period previously set in the phasing means responsive to the error;
   reference signal generating means operatively connected to the phase detection means for generating the reference signal having a reference frequency the same as one of the detection and phased frequencies; and
   adding means operatively connected to the phasing means for adding the phased detection signals phased by the phasing means as an added detection signal; and
   the phase detection means comprising a calculation unit for calculating a mutual-relation value between the one of the detection and phased detection signals and the reference signal, and an error detection unit for detecting the error responsive to the mutual-relation value.

2. An ultrasonic imaging apparatus as claimed in claim 1, wherein said reference signal generating means generates the reference signal having a reference phase corresponding to the delay period previously set in the phasing means when the phase detection means detects the error of phase between the reference signal and the detection signals output from the electroacoustic transducers.

3. An ultrasonic imaging apparatus as claimed in claim 1, wherein said reference signal generating means generates the reference signal having a reference phase corresponding to the phase period of the phased detection signals when the phase detection means detects the error of phase between the reference signal and the phased detection signals output from the phasing means.

4. An ultrasonic imaging apparatus as claimed in claim 1,
   wherein the adding means outputs an output signal corresponding to the added detection signal, and
   wherein the output signal from the adding means is used as the reference signal by the reference signal generating means.

* * * * *

UNITED STATES PATENT AND TRADEMARK OFFICE
CERTIFICATE OF CORRECTION

PATENT NO. : 5,203,336

DATED : April 20, 1993

INVENTOR(S) : Iida et al.

It is certified that error appears in the above-identified patent and that said Letters Patent is hereby corrected as shown below:

On the Title page, item [57]
In the abstract:
Line 6, "lie" should be --line--.
Col. 9, line 55, after "transducers" insert --for--.

Signed and Sealed this

First Day of February, 1994

Attest:

BRUCE LEHMAN

*Attesting Officer*    Commissioner of Patents and Trademarks